United States Patent [19]

Whitehead

[11] 4,079,739

[45] Mar. 21, 1978

[54] DIE-CUT CONTOURED CATAMENIAL NAPKIN OF MULTI-LAYERED CONSTRUCTION

[75] Inventor: Howard A. Whitehead, Appleton, Wis.

[73] Assignee: Kimberly-Clark Corporation, Neenah, Wis.

[21] Appl. No.: 754,547

[22] Filed: Dec. 27, 1976

[51] Int. Cl.² ............................................. A61F 13/16
[52] U.S. Cl. ................................ 128/290 R; 128/284; 128/290 P; 128/296; 128/287
[58] Field of Search ............... 128/284, 290 R, 290 P, 128/290 B, 268, 296

[56] References Cited

U.S. PATENT DOCUMENTS

| | | | |
|---|---|---|---|
| 1,799,147 | 4/1931 | Brisache | 128/290 B |
| 2,551,663 | 5/1951 | Fox | 128/290 R |
| 2,662,527 | 12/1953 | Jacks | 128/290 R |
| 3,867,940 | 2/1975 | Mesek | 128/287 |
| 3,881,490 | 5/1975 | Whitehead | 128/287 |
| 3,888,255 | 6/1975 | Shah et al. | 128/290 R |
| 3,916,900 | 11/1975 | Breyer et al. | 128/287 |
| 3,927,673 | 12/1975 | Taylor | 128/287 |

*Primary Examiner*—Aldrich F. Medbery

*Attorney, Agent, or Firm*—Daniel J. Hanlon, Jr.; William D. Herrick; Raymond J. Miller

[57] ABSTRACT

A die-cut, contoured, catamenial napkin of joined-together layers of sheet material assembled into a sandwich which combines a thin, soft, flexible peripheral portion for comfort with a thick central portion for increased fluid-holding capacity. The uppermost layer is a thin batt of intermingled fibers provided with unbonded low density cushion areas separated by spaced bonded areas comprised of compressed fluid-distributing channels of higher density extending generally longitudinally of the batt and intersecting the ends and edges. The central portion of the uppermost layer is upwardly deformed to provide a pad-receiving cavity in which a main fluid-holding element consisting of a relatively thick pad of absorbent material is positioned in intimate physical contact with the uppermost layer while the horizontal face portions of the side and end walls of the central pad are free of contact with neighboring components. The outer peripheral portion of the uppermost layer, and in the preferred embodiment, the lower surface of the fluid-holding element, is adhesively secured to a fluid-impervious bottom layer by a thin discontinuous film of adhesive. Pressure-sensitive adhesive may be used on the bottom of the pad for releasable attachment to a supporting undergarment.

20 Claims, 9 Drawing Figures

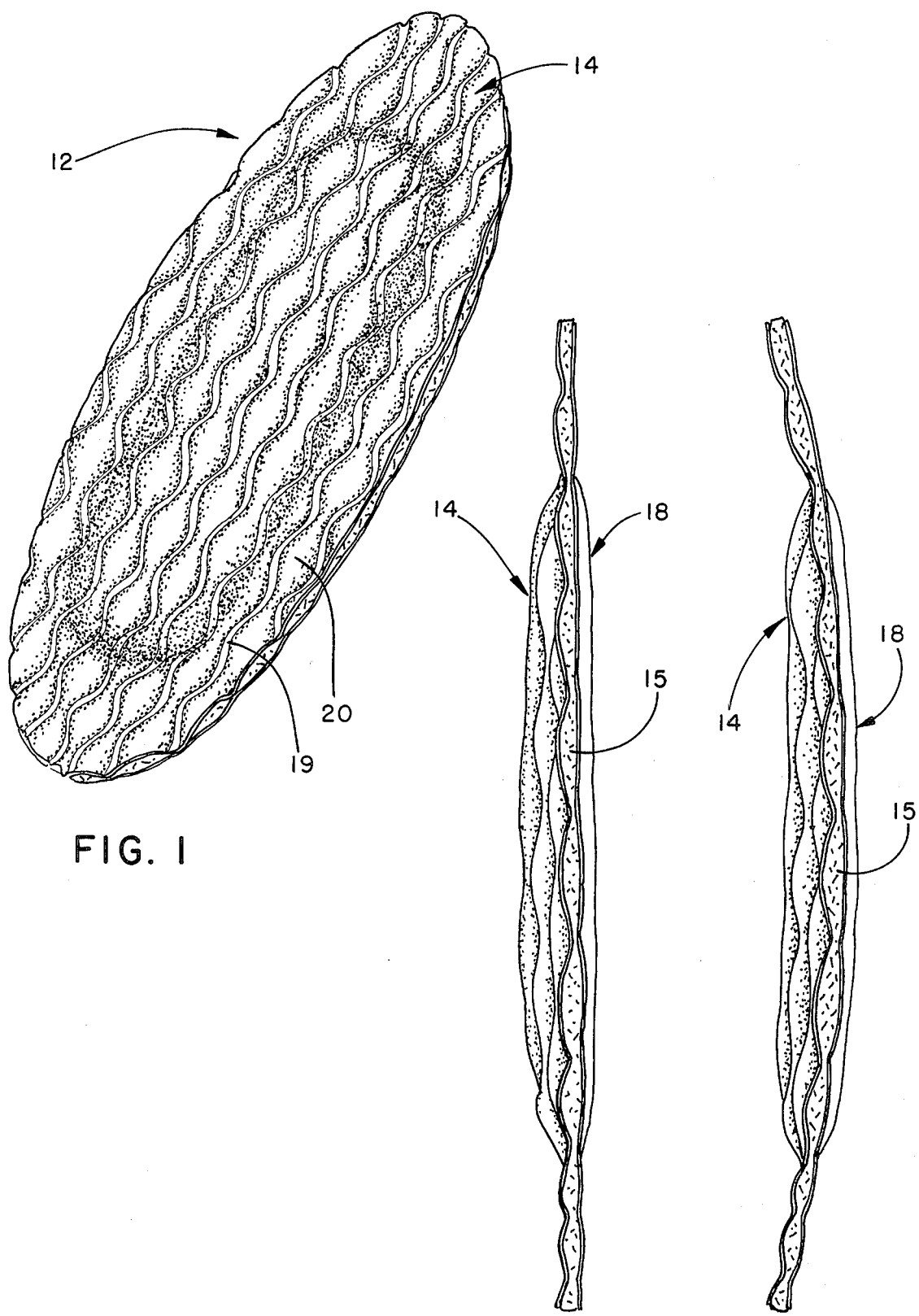

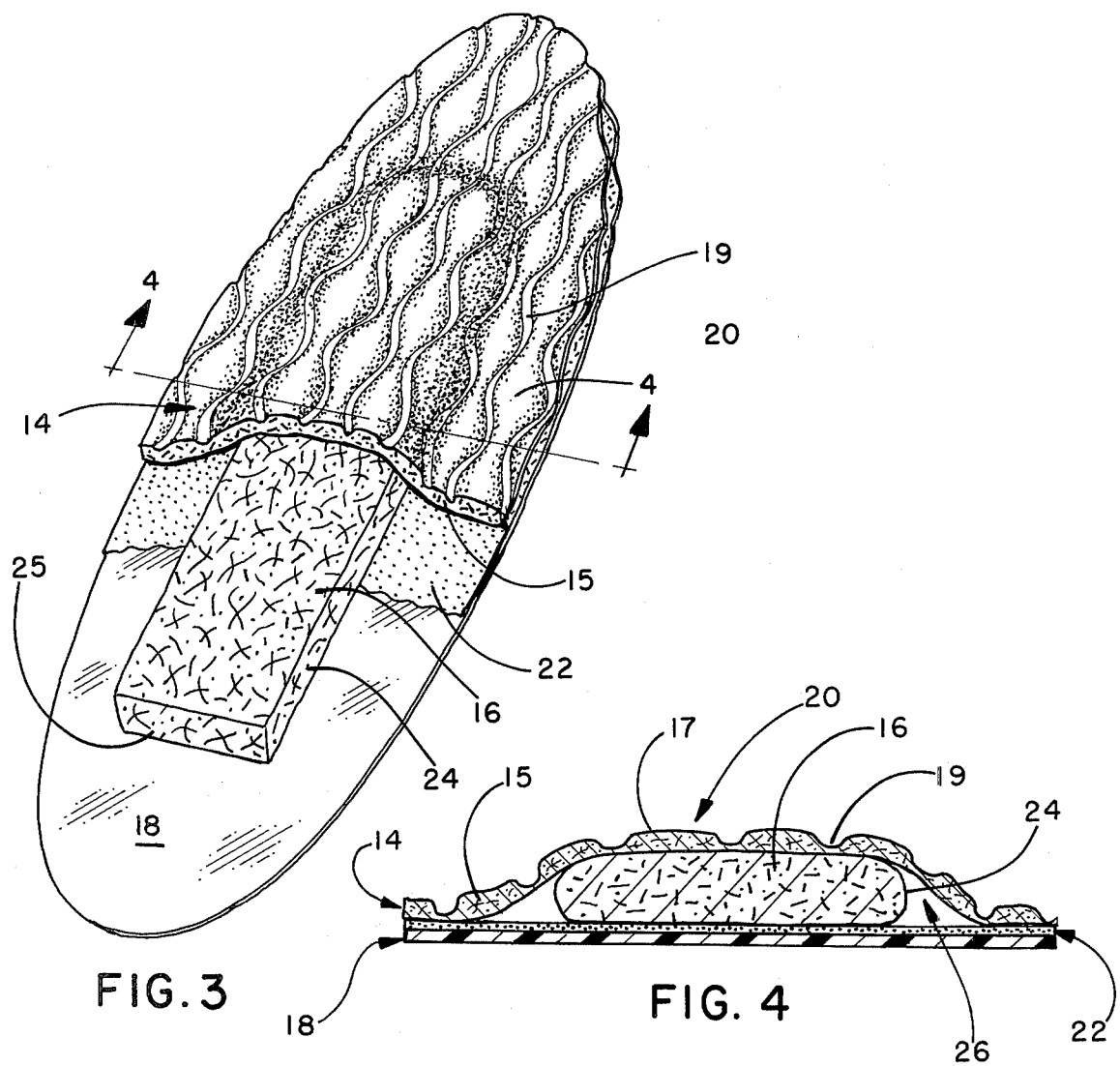
FIG. 3
FIG. 4
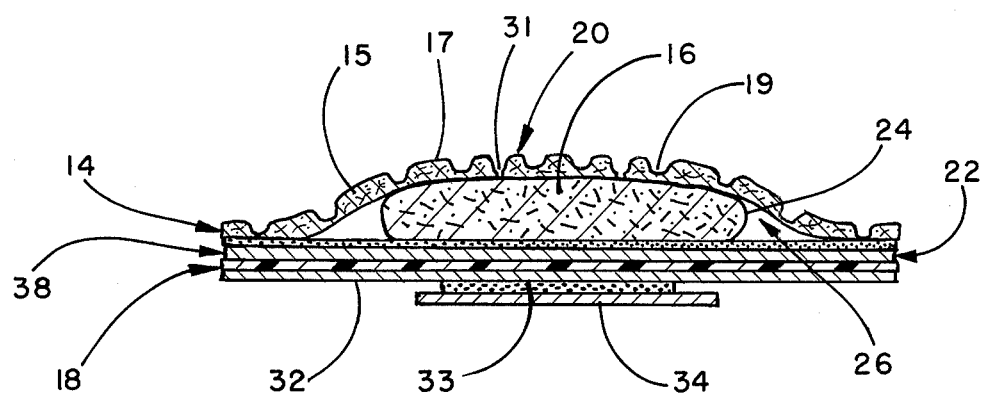
FIG. 7

DIE-CUT CONTOURED CATAMENIAL NAPKIN OF MULTI-LAYERED CONSTRUCTION

BACKGROUND OF THE INVENTION

In U.S. Pat. No. 3,881,490 of May 6,1975, to Whitehead et al there is described a very thin absorbent pad for feminine hygiene, which is intended for use as an undergarment protector between menstrual periods as well as for absorbing light flow between and during periods.

The pad as described in the patent is comprised mainly of a thin air-formed batt of short-fibered wood pulp fluff. The batt is held together primarily by hydrogen bonds provided by spaced line embossments extending generally in the longitudinal direction and intersecting the ends and edges of the batt at spaced intervals. The ends and edges are otherwise unbonded and the resulting quilt-like pillows between embossments provide the finished pad with a cushioned top and soft, flexible borders.

As indicated earlier, while such pads are intended primarily for use for absorbing light flows, or for absorbing discharges to protect undergarments from being soiled between periods, many users found the pads to be so convenient and confortable that they also employed the pads for use in absorbing all menstrual fluids during regular periods. When thus employed, it was observed that while the pads did absorb surprisingly large amounts of fluids there was a tendency for them to become soaked rapidly, permitting fluids to reach the ends and sides and causing some garment soiling. To prevent the latter situation it was necessary to make many inconvenient pad changes at short intervals. The thin pads also tended to have a wet surface feel when sudden gushes occurred, even when fluids from such gushes were eventually drawn away by the embossed lines and redistributed throughout unembossed portions of the pad.

In spite of these above-noted inconveniences, many users found these thin pads to be sufficiently confortable that they often employed the pads even during times of relatively heavy menstrual flow. Because the thin pads had these desirable characteristics, many consumer's expressed an interest in obtaining pads of similar comfort but with higher absorbent capacity.

In response to this show of interest, many attempts were made to develop a pad which would fill that need while retaining the desirable features of the thin pad, i.e. a low cost pad of unitary structure, having the same soft edges and cushioned surface, but with much higher capacity for discharged body fluids.

When attempts were made to increase capacity by making the entire pad thicker while retaining the same embossed structure as the original thin pad, it was found that the embossing pressures needed to obtain sufficient fiber bonding to arrive at the desired unitary structure gave the resulting product a stiff, boardy character which was not comfortable, which did not conform well to body contours, and which did not seat itself well in undergarments. Transfer of fluid to the sides and ends of the pad still occurred after heavy flow, and the full potential capacity of the pad was not utilized to the desired extent. The wet surface feel after long wear or sudden gushes still remained. When less pressure was used in embossing to prevent the stiff, boardy properties, the resulting pad delaminated easily during handling and use, to make it unsuitable as a potential commercial product.

In another attempt to solve the above-mentioned problems, a contoured batt was constructed having more fiber provided in the central portion to obtain a thicker center. This batt was subsequently embossed in the same manner as the original thin pads. However the variance in thickness of the starting batt did not permit good embossing without applying excessive pressure, and when the necessary high pressures were used the disadvantage of a boardy product again emerged, particularly in the thicker central portion.

In still another attempt to obtain a satisfactory product, a separately formed thin batt was embossed as in the prior art and then laminated by adhesive means to an underlying and thicker unembossed batt which was also separately formed. With this product, problems were encountered first in getting a good bonded structure in the unembossed batt without using supplementary internal adhesive. The latter created stiffness and reduced the rate of fluid penetration. Second, the resulting edges were found to be too thick, and conformability was poor.

Finally it was found that by essentially using the same basic structure as the thin pad of U.S. Pat. No. 3,884,490 for the top layer of a composite structure, deforming a central portion of that thin pad upwardly, inserting a separate thicker pad inside the hump thus formed, and adhering the outer undeformed border portion of the uppermost layer and the bottom of the insert pad to a bottom supporting layer, that a product with high capacity, with soft edges, with a dry surface feel during use, and with good conformability was obtained.

The invention described herein is directed to a sanitary napkin of the latter improved structure.

SUMMARY OF THE INVENTION

This invention is directed to a die-cut, contoured, generally oblong catamenial napkin consisting of joined-together layers of sheet material assembled into a sandwich which combines a comfortable thin, soft, flexible fluid-conducting upper layer with a narrower and shorter thick central layer of increased fluid-holding capacity and with a thin, fluid-impermeable bottom layer. The uppermost layer of the napkin is a thin batt comprised of intermingled short absorbent fibers such as wood pulp fibers, commonly called fluff, bonded together by means of a multiplicity of spaced compressed fluid-distributing channels which extend generally in the longitudinal direction of the batt and intersect the ends and edges, which provide fluffy unbonded quilt-like cushions between channels. The surface of this batt may comprise a separate thin non-woven web, or the batt fibers themselves may be bonded together by a thin discontinuous film of adhesive to provide surface integrity and scuff resistance. This uppermost layer also has its central section deformed upwardly to provide a pad-receiving cavity.

The central layer of the napkin comprises a thicker absorbent pad which is narrower and shorter than the uppermost layer and is positioned underneath the uppermost layer and disposed inside of the upwardly deformed pad-receiving cavity of the uppermost layer. The upper surface of this central pad is in intimate physical contact with the bottom surface of the uppermost layer while the outer walls or vertical face portions of the sides and edges of this central pad are free of contact with neighboring components of the napkin.

The bottom layer of the napkin is comprised of thin flexible material characterized by a resistance to fluid strike-through, and preferably is comprised of a thin fluid-impermeable film of polyethylene or similar plastic material.

In other embodiments, the bottom layer, in addition to having a thin fluid-resistant component, may also be surfaced on top with a thin batt of absorbent fibers, and/or may also be provided on its lower surface with a slip-resistant backing material such as a fibrous applique, a non-woven layer, a thin polyurethane sponge, a latex coating or the like.

The bottom layer is adhered to the underformed peripheral border area of the uppermost layer by a thin discontinuous film of adhesive, and in the preferred embodiment the bottom surface of the pad comprising the central layer is also adhered to the bottom layer by the same discontinuous film of adhesive. In the assembled napkin a space which is devoid of fiber encircles the outer boundary of the pad comprising the central layer, with said space being disposed between the vertical faces of the sides and ends of the pad comprising the central layer and the peripheral area of joinder where the uppermost layer is adhered to the bottom layer.

The assembled multi-layered napkin described above preferably has at least one area of pressure-sensitive adhesive disposed on its bottom surface for releasable attachment to a supporting undergarment.

In still another embodiment, the assembled napkin is constructed with an arcuate slightly concave contour in the long direction for better conformability when worn.

The above and other embodiments and advantages of the invention will become apparent by reference to the accompanying drawings and following detailed description.

BRIEF DESCRIPTION OF THE DRAWINGS

In the drawings:

FIG. 1 is a perspective top view of a contoured catamenial napkin in accordance with this invention.

FIG. 2 is a side view of the napkin of FIG. 1.

FIG. 2A is a side view of a slightly modified napkin and similar to FIG. 2 except that it is concavely arcuate in shape.

FIG. 3 is a view similar to FIG. 1 but having a portion cut away to show the inner construction.

FIG. 4 is an enlarged section taken through line 4—4 of FIG. 3.

FIG. 7 is an enlarged section taken through line 7—7 of FIG. 6.

DETAILED DESCRIPTION OF THE DRAWINGS AND PREFERRED EMBODIMENTS

Figures 5, 6:
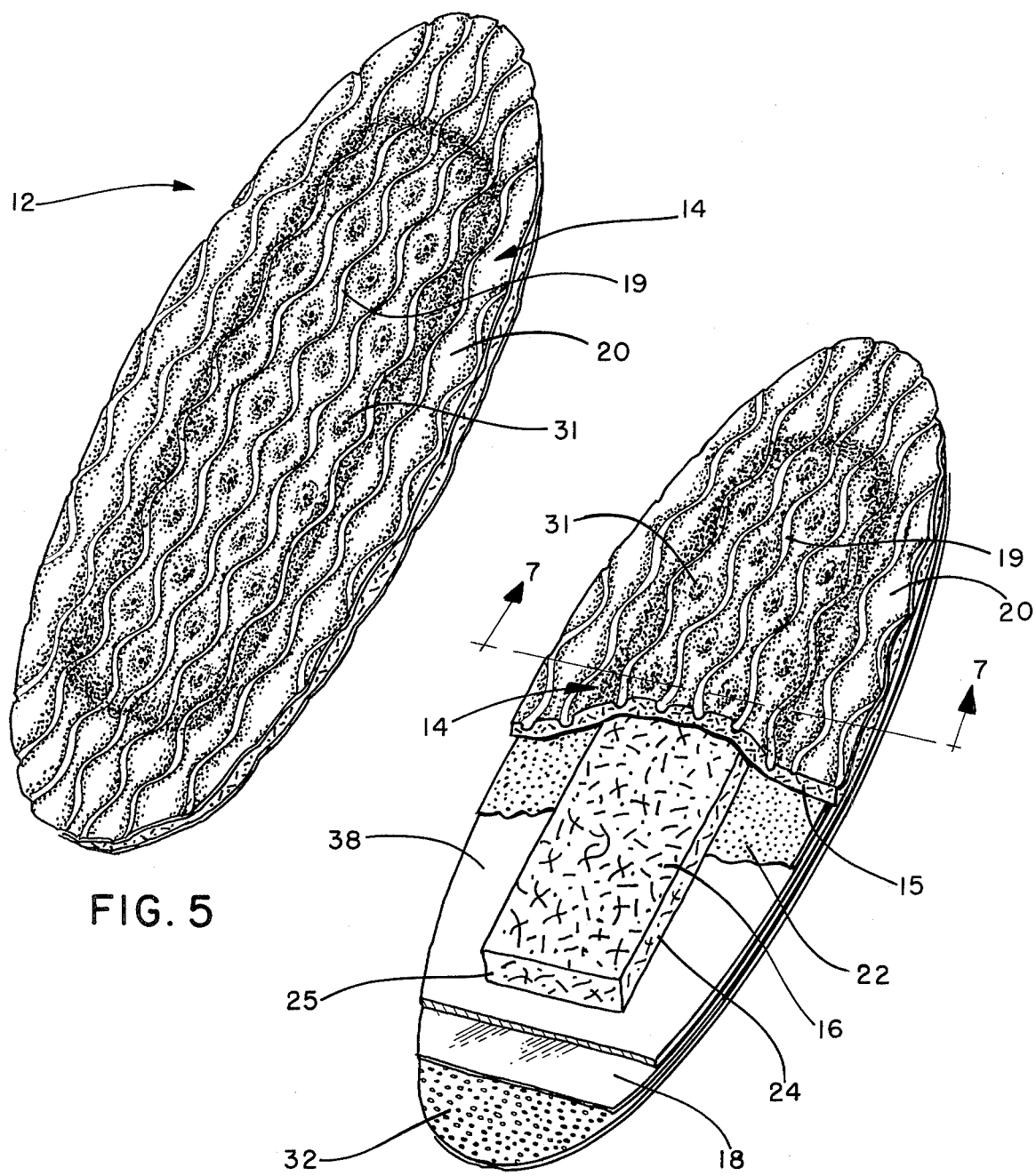
FIG. 5 is a perspective top view of another embodiment of a contoured catamenial napkin in accordance with this invention.
FIG. 6 is a view of an embodiment similar to FIG. 5 but having a portion cut away to show an inner structure with a number of optional features.

In presenting the details of a preferred embodiment of a multi-layered sanitary napkin in accordance with this invention reference is first made to FIGS. 1 - 4 of the drawings.

As shown in these drawings, die-cut and contoured sanitary napkin 12 is comprised of three joined-together layers of sheet material consisting of an elongate uppermost body-contacting layer 14; a thicker central layer 16 which is shorter and narrower than uppermost layer 14, and a thin bottom layer 18 which is resistant to fluid strike-through.

Uppermost layer 14 is comprised of a thin batt of intermingled absorbent fibers 15 such as wood fluff, and has a scuff-resistant top surface 17. The latter scuff-resistant surface 17 may be provided by bonding the surface fibers of the batt itself with a suitable bonding agent, or it may consist of a separate fluid-pervious non-woven web.

Uppermost layer 14 has impressed into its surface a plurality of spaced channels 19 of compacted fibers extending in a generally longitudinal direction for the full length of the batt and intersecting the edges and ends of the batt at spaced intervals. Compressed channels 19 which are comprised of compacted fibers bonded to each other primarily by hydrogen bonds, created in the known manner through the use of pressure and a suitable moisture content, provide the uppermost layer with a plurality of high capillarity conduits through which, because of the small pore size created by compaction as is well known in the art, fluid will travel at a faster rate than the intervening uncompressed areas 20. Uncompressed areas 20 also provide fluffy unbonded quilt-like cushions in the spaces between channels.

While the compressed channels are shown as uniformly spaced and substantially parallel line embossments, other longitudinally extending patterns may be used. Undulating or wavy line patterns are preferred because when the napkin is bent during use, wavy or undulating lines were found to flex more readily than straight lines.

As shown particularly in FIGS. 3 and 4, the centrally located portion of uppermost layer 14 is upwardly deformed to define an elongate pad-receiving cavity in which a thick pad of absorbent material identified as central layer 16 is disposed.

The pad comprising the central layer may comprise any of the well-known materials used in absorbent pads including wood pulp fluff, multiple layers of cellulose wadding, cotton or rayon fibers, cellulose sponge, hydrophilic synthetic sponge such as polyurethane, and the like.

Bottom layer 18, which in this embodiment is shown as a thin plastic film, is coextensive with uppermost layer 14 and is adhered to layer 14 by a discontinuous film of adhesive 22 in the areas where bottom layer 18 and uppermost layer 14 are in face to face contact around the external boundaries of the batt which comprises central layer 16.

As indicated particularly in FIG. 4, the upper surface of central layer 16 is in intimate contact with the bottom surface of uppermost layer 14, and an airspace 26 is provided, at the sides of the pad comprising the central layer, between sidewalls 24 of central layer 16 and the line of contact where the peripheral areas of uppermost layer 14 and bottom layer 18 meet and are joined outside the boundaries of central layer 16. A similar airspace exists adjacent the end walls 25 of the central layer so that the airspace encircles the entire central layer.

As indicated in the drawings, central layer 16 is also secured to bottom layer 18 by discontinuous film of adhesive 22. While this is the preferred embodiment it is not essential that central layer 16 be thus secured to the bottom layer as long as the bottom layer and uppermost layer are secured to each other in the peripheral areas extending all the way around central layer 16.

In either case, the upper surface of central layer 16 should not be secured to the bottom surface of the uppermost layer because this detracts from the conformability of the napkin when in place against the body. Such securement is also somewhat detrimental to obtaining the desirable rapid transfer of absorbed fluids to the central layer from the uppermost layer. In addition, the concavely arcuate configuration shown in the FIG. 2A modification and later described is more easily obtained when there is no adhesive securement of the top surface to the uppermost layer.

Airspace 26, which is provided between the faces of sidewalls 24 and end walls 25 of the central layer 16 and the line of joinder where uppermost layer 14 and bottom layer 16 meet, performs an important function in use. After menstrual fluid strikes the surface of the assembled pad, the force of gravity tends to cause the fluid to migrate selectively downward into central layer 16 and because airspace 26 insulates layer 16 from physical contact with the peripheral-areas of the finished napkin, the absorbed fluid is confined, and more or less trapped, within central layer 16, thus substantially preventing fluid transfer to the edges or ends of the napkin which avoids staining. Such confinement of absorbed fluids is accomplished without treating the peripheral edges of the napkin with water-repellants, or without using fluid barriers adjacent the edges, both of which are common methods employed to prevent edge staining in more conventional napkins.

The embodiments shown in FIGS. 5-7 illustrate several other modifications of a sanitary napkin made in accordance with this invention. In these figures, like numbers are used to identify like elements as shown in FIGS. 1-4, and a description of these elements will not be repeated here. The various modifications or new features not shown in the earlier described embodiment of FIGS. 1-4 are identified by numbers in the 30 series in the following description.

In the development of this improved sanitary napkin it was found that while the new napkin did have much higher capacity and successfully confined most of the absorbed fluid within the structure of central layer 16 it was also found to be desirable to obtain more rapid transfer of menstrual fluid from the surface of the napkin to the central layer, particularly when the fluid first makes contact with the napkin in the raised cushioned areas of the surface rather than at the compacted fluid-conducting channels.

It was found that this improved transfer can be achieved by providing the uppermost layer with spaced funnel-shaped apertures 31 disposed in the central area of the raised cushioned areas 20 to provide direct communication with the central layer. With apertures present, fluid which is deposited at, or near to, the apertures rapidly migrates by gravity into the central layer 16 and helps maintain a perceivably drier surface than when the apertures 31 are not employed. While the apertures are not essential, some functional advantages are obtained.

Some additional capacity is also obtained by adding a thin fiber batt on the surface of the bottom layer as shown at 38.

In another feature, it was found that the napkin was perceived by the user of being more aesthetic and providing the appearance of more potential comfort when a low reflectance surface, which incidentally has a higher coefficient of friction, is added to the bottom surface as shown at 32. Such kind of surface may be provided by using an applique of fibers, by flocking, by applying various non-woven webs, or by using a thin layer of sponge. Each of these surfaces were found acceptable to users in varying degrees.

Another feature, mentioned earlier in this specification and which is useful in connection with this invention is the provision of a pressure-sensitive adhesive means on the bottom of the napkin for attachment to a supporting undergarment. Such adhesive means is shown at 33, covered by a conventional removable protective sheet 34. The use of such an attachment system and a number of variations thereof are well known in the art and is merely mentioned here as a useful modification of the napkin defined herein. It is also understood that such pressure sensitive adhesive means may be used in constructions shown in FIGS. 1 – 4 which do not have the additional layers 32 and 38 shown in FIGS. 6 and 7.

Figure 8:
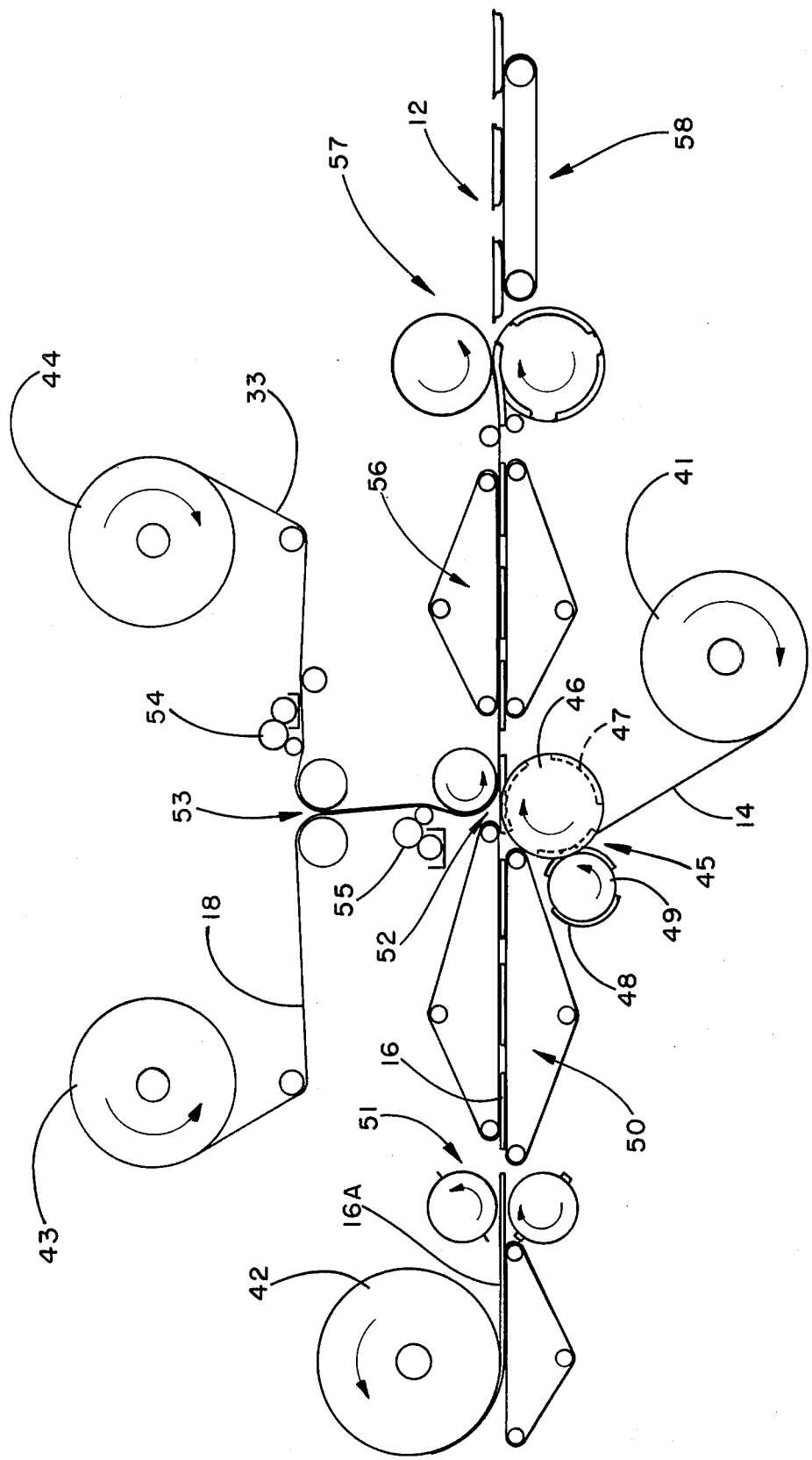
FIG. 8 is a schematic illustration of apparatus suitable for manufacturing a multi-layered sanitary napkin in accordance with this invention.

Another advantage of the improved napkin of this invention is the fact that it adapts itself to low cost, high speed production. FIG. 8 shows in schematic form a suitable apparatus which may be used for such production. As shown therein, the rolls of material used to supply the various layers in the napkin structure are pre-manufactured, although an in-line system for such manufacture is also considered feasible. In FIG. 8, supply roll 41 comprises the pre-embossed uppermost layer 14 of the napkin, supply roll 42 is the central layer 14, supply roll 43 is the bottom layer 18 and supply roll 44 is the pressure-sensitive adhesive and protective sheet for the adhesive.

The manufacturing operation may be carried out somewhat as follows:

Pre-embossed uppermost layer 14 is fed from supply roll 41 through a forming nip 45 in which a female roll 46 is provided with a suitably shaped elongate cavities 47. In forming nip 45, layer 14 is pressed into cavity 47 by a matching raised portion 48 of male roll 49. This operation impresses into uppermost layer 14 an upwardly deformed cavity.

At the same time, the material for thick central layer 16a is fed between rotating cutter rolls 51, where it is cut into suitable length pads 16. The central layer pads 16 are fed onto traveling belt section 50 from where pads 16 are deposited into the preformed cavity of the uppermost layer 14 at nip 52.

Meanwhile, bottom layer 18 is fed from roll 43 through nip 53 where it is joined together with a continuous strip of pressure-sensitive material 33 fed from roll 44. The pressure-sensitive strip may be two-sided and directly adhered to the bottom layer by its own adhesive power, or it may be one-sided in which case adhesive is applied at station 54 to provide securement to the bottom side of bottom layer 18. The top surface of bottom layer 18 then has applied thereto a discontinuous film of adhesive at station 55. A preferred adhesive for this purpose is a hot melt type although other suitable adhesives may be used. The adhesive may be applied over the entire top surface of layer 18, or it may be applied in a patterned arrangement which matches peripheral portions of the bottom layer which will lie outside the outer boundaries of central layer 16 when all napkin components are assembled.

Deformed uppermost layer 14 containing the cut to size pad of central layer 16, and the adhesive-coated bottom layer 18 with the pressure sensitive strip in place, are pressed together at nip 52 to seal together the peripheral portion of uppermost layer 14 and bottom layer 18 around central layer 16, and the sandwich is then passed by means of belt conveyor section 56 to a die-cutting tool 57 which stamps out the finished napkin in the desired shape and size. A suitable conveyor 58 is then used to transfer the finished napkins 12 to a packaging station.

In manufacturing these napkins it was found that if the uppermost layer 14 is supplied to nip 52 at higher tension than the bottom layer 18, the finished napkin will assume a concave arcuate shape in the long direction as shown in FIG. 2A after tension is relieved by the die-cutting operation. The fact that the central pad is not adhered to the uppermost layer apparently assists in permitting the finished napkin to assume this shape more readily. The degree of curvature can also be controlled by the amount of tension applied on the uppermost layer during manufacture. In the finished arcuately concave napkin the outer edges of uppermost layer 14 are still coterminous with the outer edges of bottom layer 18, but uppermost layer is slightly shorter in its longitudinal dimension than the bottom layer. This shorter dimension of the upper layer is provided when the manufacturing operation is carried out in a manner where the uppermost layer is under greater tension than the remaining components. The upper layer is thus in stretched condition at the time of joining, and the uppermost layer and bottom layer are therefore of the same length at the time. After die-cutting, when tension is no longer present, the uppermost layer contracts to a shorter untensioned length to provide the arcuate shape.

What is claimed is:

1. A die-cut catamenial napkin of generally oblong shape consisting of a unified, surface-contoured sandwich of joined-together layers comprising:
  a. an uppermost body-contacting absorbent layer adapted to receive and distribute discharged body fluids;
  b. a central layer comprised of a main fluid-holding element of absorbent material; and
  c. a bottom layer comprised of a flexible material which resists fluid strike-through;
  said uppermost absorbent layer being comprised of a thin batt of intermingled absorbent fibers, said batt having a fluid-pervious scuff-resistant facing, said batt having impressed therein a plurality of spaced fluid-spreading channels defining compacted areas extending in a generally longitudinal direction for the full length of the batt to intersect the edges and ends of the batt at spaced intervals, said channels being comprised of fibers bonded to each other in the compacted area, the fibers in said batt disposed under said facing and disposed in the spaces between said channels being substantially unbonded to each other;
  said uppermost layer having a central portion upwardly deformed to define an elongate pad-receiving cavity;
  said central layer and main fluid-holding element being comprised of a pad of absorbent material, said pad being narrower and shorter than said body-contacting layer, said pad being disposed inside the elongate pad-receiving cavity of said uppermost layer with the upper surface of said pad being in intimate physical contact with but unadhered to the bottom surface of said uppermost layer;
  said bottom layer having at least one face which is fluid-impervious;
  the peripheral edges of said uppermost layer and said bottom layer being die-cut and coterminous;
  and the lower surface of said uppermost layer being joined to the upper surface said bottom layer by means of a discontinuous film of adhesive disposed between said uppermost and bottom layers in the peripheral areas lying outside of the boundaries of said central element where said uppermost and bottom layers are in contact with each other.

2. The napkin of claim 1 wherein the pad of said central layer is also adhesively secured to said bottom layer by a discontinuous film of adhesive.

3. The napkin of claim 1 wherein a plurality of spaced funnel-shaped apertures are provided in the face of said uppermost layer in the unbonded areas disposed between said fluid-spreading channels and at least in the area overlying said central layer.

4. The napkin of claim 3 wherein said funnel-shaped apertures are disposed only in the area overlying said central layer.

5. The napkin of claim 3 wherein said funnel-shaped apertures are in communication with said central layer.

6. The napkin of claim 1 wherein the fluid-impervious bottom layer has an additional thin batt of absorbent fibers disposed on the top surface of said bottom layer.

7. The napkin of claim 1 wherein the fluid-impervious bottom layer has a material with a higher coefficient of friction disposed on the bottom surface of said bottom layer.

8. The napkin of claim 6 wherein the fluid-impervious bottom layer has a material with a higher coefficient of friction disposed on the bottom surface of said bottom layer.

9. The napkin of claim 1 wherein said uppermost layer and said bottom layer are coterminous at the peripheral edges but wherein said uppermost layer has a shorter longitudinal dimension than said bottom layer to provide said napkin with an arcuately concave configuration in the long direction.

10. The napkin of claim 6 wherein said uppermost layer and said bottom layer are coterminous at the peripheral edges but wherein said uppermost layer has a shorter longitudinal dimension than said bottom layer to provide said napkin with an arcuately concave configuration in the long direction.

11. The napkin of claim 7 wherein said uppermost layer and said bottom layer are coterminous at the peripheral edges but wherein said uppermost layer has a shorter longitudinal dimension than said bottom layer to provide said napkin with an arcuately concave configuration in the long direction.

12. The napkin of claim 8 wherein said uppermost layer and said bottom layer are coterminous at the peripheral edges but wherein said uppermost layer has a shorter longitudinal dimension than said bottom layer to provide said napkin with an arcuately concave configuration in the long direction.

13. The napkin of claim 1 wherein the lower surface of the bottom layer has pressure sensitive means applied thereto for use in attaching said napkin to a supporting undergarment.

14. The napkin of claim 6 wherein the lower surface of the bottom layer has pressure sensitive means applied thereto for use in attaching said napkin to a supporting undergarment.

15. The napkin of claim 7 wherein the lower surface of the bottom layer has pressure sensitive means applied thereto for use in attaching said napkin to a supporting undergarment.

16. The napkin of claim 8 wherein the lower surface of the bottom layer has pressure sensitive means applied thereto for use in attaching said napkin to a supporting undergarment.

17. The napkin of claim 9 wherein the lower surface of the bottom layer has pressure sensitive means applied thereto for use in attaching said napkin to a supporting undergarment.

18. The napkin of claim 10 wherein the lower surface of the bottom layer has pressure sensitive means applied thereto for use in attaching said napkin to a supporting undergarment.

19. The napkin of claim 11 wherein the lower surface of the bottom layer has pressure sensitive means applied thereto for use in attaching said napkin to a supporting undergarment.

20. The napkin of claim 12 wherein the lower surface of the bottom layer has pressure sensitive means applied thereto for use in attaching said napkin to a supporting undergarment.

* * * * *